United States Patent
Ryu et al.

(10) Patent No.: US 11,147,807 B2
(45) Date of Patent: Oct. 19, 2021

(54) PHARMACEUTICAL COMPOSITION CONTAINING DUSP1 INHIBITOR

(71) Applicants: INDUSTRY-UNIVERSITY COOPERATION FOUNDATION HANYANG UNIVERSITY, Seoul (KR); KOREA RESEARCH INSTITUTE OF CHEMICAL TECHNOLOGY, Daejeon (KR)

(72) Inventors: Seong Eon Ryu, Seoul (KR); Tae Hyun Park, Seoul (KR); Kwang Hwan Lee, Seoul (KR); Ju Seop Kang, Seoul (KR); Shin Hee Kim, Seoul (KR); Kyoung Tae Nam, Seoul (KR); Hyeon Kyu Lee, Daejeon (KR)

(73) Assignees: INDUSTRY-UNIVERSITY COOPERATION FOUNDATION HANYANG UNIVERSITY, Seoul (KR); KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 97 days.

(21) Appl. No.: 16/603,993

(22) PCT Filed: Feb. 28, 2018

(86) PCT No.: PCT/KR2018/002477
§ 371 (c)(1),
(2) Date: Oct. 9, 2019

(87) PCT Pub. No.: WO2018/190511
PCT Pub. Date: Oct. 18, 2018

(65) Prior Publication Data
US 2020/0155537 A1    May 21, 2020

(30) Foreign Application Priority Data
Apr. 10, 2017   (KR) .................. 10-2017-0046102

(51) Int. Cl.
*A61K 31/47*    (2006.01)
*A61P 25/24*    (2006.01)
*A61P 35/00*    (2006.01)

(52) U.S. Cl.
CPC .............. *A61K 31/47* (2013.01); *A61P 25/24* (2018.01); *A61P 35/00* (2018.01)

(58) Field of Classification Search
CPC .......... A61K 31/47; A61P 25/24; A61P 35/00; Y10S 514/893
(Continued)

(56) References Cited

U.S. PATENT DOCUMENTS

| 2004/0198716 | A1 | 10/2004 | Arad et al. |
| 2010/0120849 | A1* | 5/2010 | Chung et al. .......... A61K 31/47 514/312 |
| 2016/0214940 | A1 | 7/2016 | Conn et al. |

FOREIGN PATENT DOCUMENTS

| KR | 10-2009-0058967 A | 6/2009 |
| KR | 10-0916160 B1 | 9/2009 |

(Continued)

OTHER PUBLICATIONS

Yunchun Chen et al., "Microinjection of sanguinarine into the ventrolateral orbital cortex inhibits Mkp-1 and exerts an antidepressant-like effect in rats", Neuroscience Letters, 2012 pp. 327-331, vol. 506.

(Continued)

*Primary Examiner* — Taylor V Oh
(74) *Attorney, Agent, or Firm* — Sughrue Mion, PLLC

(57) ABSTRACT

The present invention relates to a pharmaceutical composition comprising a DUSP1 inhibitor. The pharmaceutical composition comprising the DUSP1 inhibitor according to the present invention can solve the problems of inhibitors that target the active site because it inhibits DUSP1 by an (Continued)

allosteric inhibitory mechanism, and is effective for preventing or treating diseases involving DUSP1 enzymes, for example, a cancer such as a liver cancer, a breast cancer and a pancreatic cancer, a hepatitis C, and a depression. In particular, the DUSP1 inhibitor according to the present invention is very effective in treating a depression because it directly acts on neuronal growth.

6 Claims, 4 Drawing Sheets

(58) Field of Classification Search
USPC .......................................................... 514/312
See application file for complete search history.

(56) References Cited

FOREIGN PATENT DOCUMENTS

| KR | 10-1335458 B1 | 12/2013 |
| KR | 10-2015-0083353 A | 7/2015 |
| WO | 2000/068202 A1 | 11/2000 |
| WO | 2005/099688 A2 | 10/2005 |
| WO | WO 2012/093741 A * | 7/2012 |
| WO | 2015/187496 A1 | 12/2015 |
| WO | 2016/114655 A1 | 7/2016 |

OTHER PUBLICATIONS

Ho Kyung Seo et al., "Antitumor activity of the c-Myc inhibitor KSI-3716 in gemcitabine-resistant bladder cancer", Oncotarget, 2014, pp. 326-337, vol. 5, No. 2.

Kyung-Chae Jeong et al., "Small-molecule inhibitors of c-Myc transcriptional factor suppress proliferation and induce apoptosis of promyelocytic leukemia cell vial cell cycle arrest", Molecular Biosystems, 2010, pp. 1503-1509, vol. 6.

Jung Eun Choi et al., "Suppression of Dual Specificity Phosphatase I Expression Inhibits Hepatitis C Virus Replication", PloS One, Mar. 2015, pp. 1-11, vol. 10, No. 3.

Kyung-Chae Jeong et al., "Intravesical Instillation of c-MYC Inhibitor KSI-3716 Suppresses Orthotopic Bladder Tumor Growth", The Journal of Urology, Feb. 2014, pp. 510-518, vol. 191.

International Search Report for PCT/KR2018/002477 dated Jun. 21, 2018 (PCT/ISA/210).

* cited by examiner (FIG. 1)
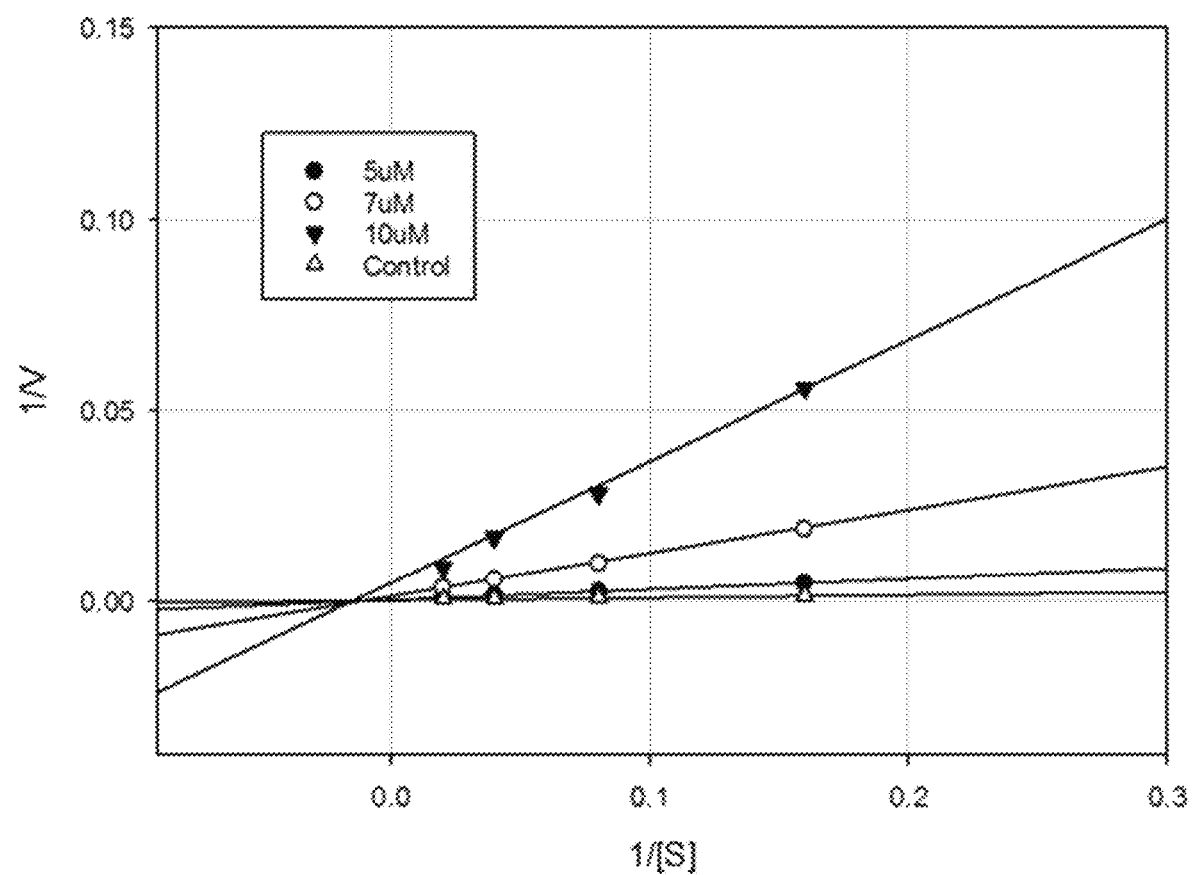

(FIG. 2)
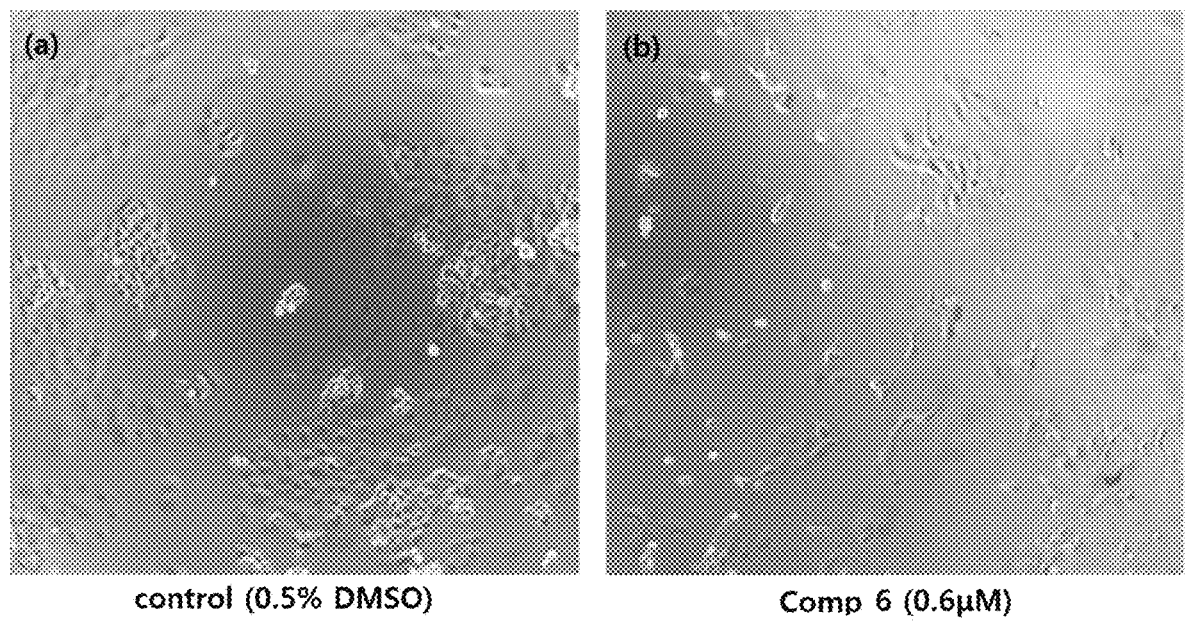

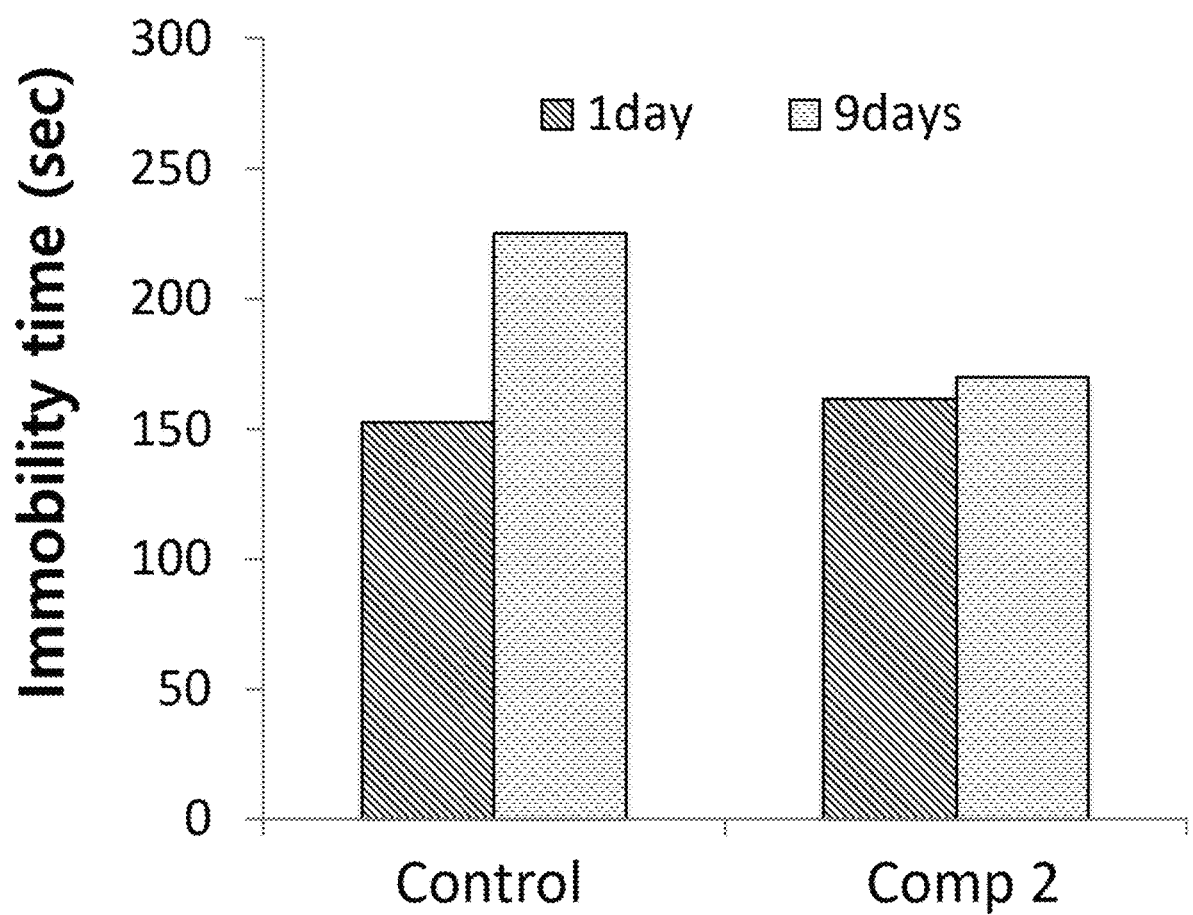
(FIG. 3)

(FIG. 4)
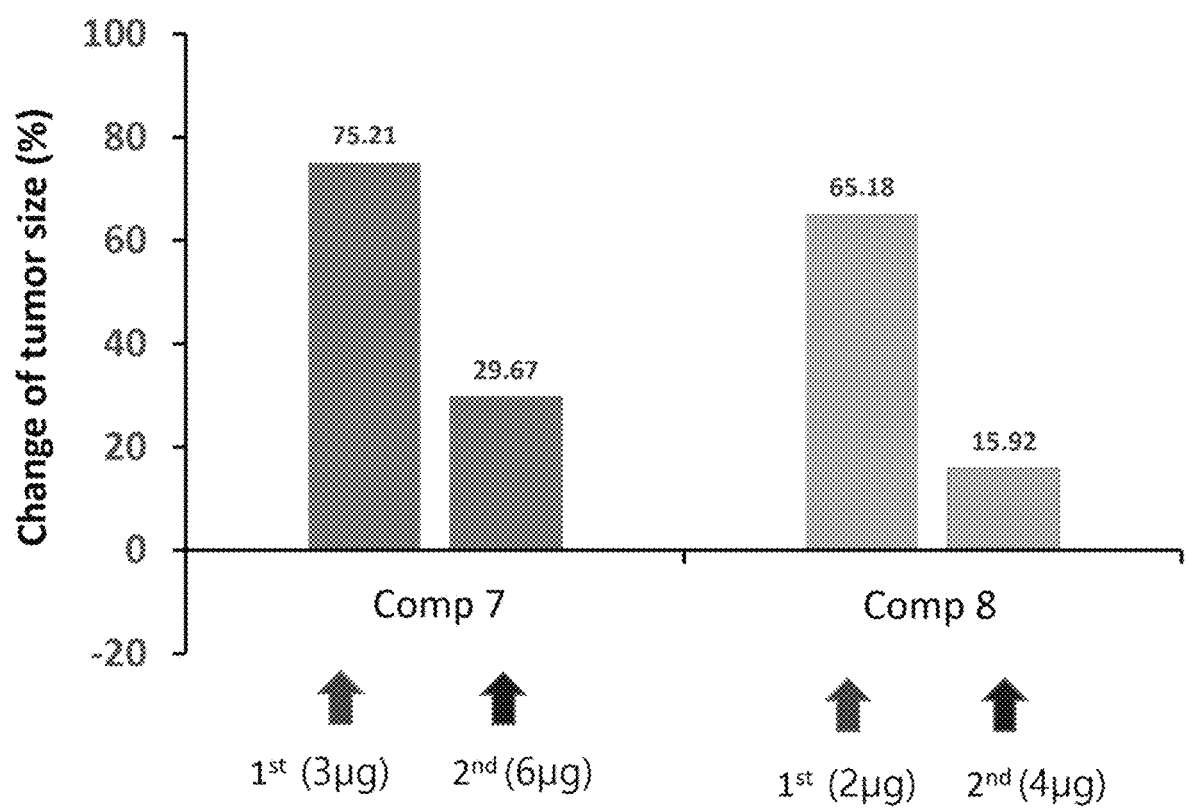

PHARMACEUTICAL COMPOSITION CONTAINING DUSP1 INHIBITOR

CROSS REFERENCE TO RELATED APPLICATIONS

This application is a National Stage of International Application No. PCT/KR2018/002477 filed Feb. 28, 2018, claiming priority based on Korean Patent Application No. 10-2017-0046102 filed Apr. 10, 2017.

TECHNICAL FIELD

The present invention relates to a pharmaceutical composition comprising a DUSP1 inhibitor, and more particularly, to a pharmaceutical composition for preventing and treating a depression, a hepatitis C and a cancer, which comprises a DUSP1 protein activity inhibitor containing 4-quinolinone derivative as an effective ingredient.

BACKGROUND

Phosphorylation of a protein plays a key role in regulating various cellular phenomena such as a cell growth, a differentiation, an immune response, and a brain function. Improper phosphorylation of the protein may lead to a variety of diseases, for example, a cancer, diabetes, an immune disease, a nervous system disease, etc. may occur due to improper regulation of the protein phosphorylation.

Therefore, attempts have been made to develop protein kinases and protein phosphatases that regulate the protein phosphorylation and dephosphorylation as a target protein for the treatment of the diseases, and the inhibitors of the protein kinases have already been clinically proven to be effective in treating the above diseases. In recent years, researches have been actively conducted to develop therapeutic agents of the diseases targeting the protein phosphatases.

Dual specificity protein phosphatase 1 (DUSP1) which belongs to a family of protein tyrosine phosphatases (PTP) has been known to selectively degrade the phosphate groups of ERK proteins in cells to regulate ERK signal transfer. It has been also known that the DUSP1 plays an important role not only in the treatment of cancers such as a breast cancer, a pancreatic cancer, a liver cancer, etc., but also in the treatment of a hepatitis C and a depression.

Specifically, Candis et al., (2014) Mitochondrial MKP1 Is a Target for Therapy-Resistant HER2-Positive Breast Cancer Cells, *Cancer Res.*, 74, 7498-7509 has demonstrated that Mitochondrial DUSP1 (MKP1) is the target of therapy-resistant HER2-positive breast cancer cells and confirmed that a combination of DUSP1 and Her2 inhibitors is effective in treating a breast cancer.

In addition, Liu et al., (2014) DUSP1 Is a Novel Target for Enhancing Pancreatic Cancer Cell Sensitivity to Gemcitabine, *Plos One*, 9, e84982 has found that DUSP1 is overexpressed in a pancreatic cancer cell and reported that the inhibition of DUSP1 by using shRNA reduces the resistance to gemcitabine, an anticancer drug, and significantly increases the effect of inhibiting cancer cell growth.

Choi et al., (2014) Suppression of Dual Specificity Phosphatase I Expression Inhibits Hepatitis C Virus Replication, *Plos One* 10, e0119172 has found that DUSP1 is overexpressed in a patient with a chronic hepatitis C and predicted that a combined use of interferon and DUSP1 inhibitor in the treatment of a hepatitis C would have a synergistic effect.

Duric et al., (2010) A negative regulator of MAP kinase causes depressive behavior, *Nature Medicine* 16, 1328-1332 has found that DUSP1 is overexpressed in the brains of experimental mice suffering from a depressive symptom after repeated stresses in the mice and established that the mice lacking the DUSP1 gene have a superior ability to fight the stress. Further, Chen et al., (2012) Microinjection of sanguinarine into the ventrolateral orbital cortex inhibits Mkp-1 and exerts an antidepressant-like effect in rats, *Neurosci Lett* 506, 327-331 has showed that anti-depressant effects similar to those of the conventional anti-depressants are observed when sanguinarine known as a selective inhibitor of DUSP1 is injected into the ventrolateral orbital cortex of experimental rats.

As described above, although inhibition of the DUSP1 is known to be effective in treating diseases such as a breast cancer, a pancreatic cancer, a hepatitis C, and a depression, there have been no clinically successful therapeutic agents reported in the field of developing therapeutic agents targeting PTP. The conventional development of PTP inhibitor mainly targets the active site of a PTP enzyme, and, since the PTP active site pocket has a relatively low depth and few parts that can interact strongly with the inhibitor compound, it is very difficult to optimize the targeted compounds in terms of inhibition potency of enzyme function, selectivity, permeability of a cell membrane, etc.

In order to overcome this problem, efforts have recently been made to use compounds having an allosteric inhibitory effect. Methods for the allosteric inhibition include the use of pockets between domains, the use of fluidity of D-loops in active pocket sites, and the use of atypical parts at the ends of active site domains. In the case of the inhibitors discovered using such allosteric approaches, it is expected that the problem of targeting the active site can be solved.

Meanwhile, a depression has a high incidence (~16%) throughout life and a tremendous economic burden (more than 100 trillion won per year) all over the world. Currently, the market for these therapeutic agents is about 11 trillion won, and the market is growing rapidly. Even in Korea, the prevalence rate is 5.6% and the annual increase rate is 2.5%. Currently, the anti-depressant most widely used is the SSRI (selective serotonin reuptake inhibitor) family that regulates the resorption of serotonin, and the representative examples thereof include Prozac and Paxil. Recently, there have been attempts to use ketamine, an anesthetic for humans and animals, as an anti-depressant. However, since these conventional therapeutic agents do not act directly on the target, there are problems that not only take a long time to show the effects, but also have side effects such as suicidal thoughts.

Further, deaths caused by a cancer are 7.6 million which correspond to 17% of global deaths and are expected to surge to 11.4 million by 2030. The cancer remains the number one cause of death in Korea, and according to the analysis of the 'EDI claims by drug efficacy' of the Korea Health Insurance Review & Assessment Service, 533.3 billion won is charged for anti-malignant tumor drugs. Furthermore, the development of effective prevention and treatment of the cancer is very urgent due to the huge social costs.

Thus, the present inventors have found novel compounds that can inhibit the activity of DUSP1 in an allosteric inhibitory manner, and this invention has been completed by confirming that this compound can be used for the prevention or treatment of a depression, a hepatitis C and a cancer.

DETAILED DESCRIPTION OF THE INVENTION

Technical Problem

An object of the present invention for solving the above problems is to provide a pharmaceutical composition for preventing or treating a depression, which comprises a DUSP1 inhibitor as an effective ingredient.

Another object of the present invention is to provide a pharmaceutical composition for preventing or treating a hepatitis C, which comprises a DUSP1 inhibitor as an effective ingredient.

Still another object of the present invention is to provide a pharmaceutical composition for preventing or treating a cancer, which comprises a DUSP1 inhibitor as an effective ingredient.

Technical Solution

In order to achieve the above objects, the present invention provides a pharmaceutical composition for preventing or treating a depression, which comprises a DUSP1 inhibitor as an effective ingredient.

The present invention also provides a pharmaceutical composition for preventing or treating a hepatitis C, which comprises a DUSP1 inhibitor as an effective ingredient.

The present invention also provides a pharmaceutical composition for preventing or treating a cancer, which comprises a DUSP1 inhibitor as an effective ingredient.

In addition, the present invention provides a method for treating a depression, which comprises administering a DUSP1 inhibitor to an animal suffering from the depression.

Further, the present invention provides a method for treating a hepatitis C, which comprises administering a DUSP1 inhibitor to an animal suffering from the hepatitis C.

Furthermore, the present invention provides a method for treating a cancer, which comprises administering a DUSP1 inhibitor to an animal suffering from the cancer.

In the present invention, the cancer may be a liver cancer, a breast cancer or a pancreatic cancer.

In the present invention, the DUSP1 inhibitor may comprises a compound represented by Formula 1:

[Formula 1]

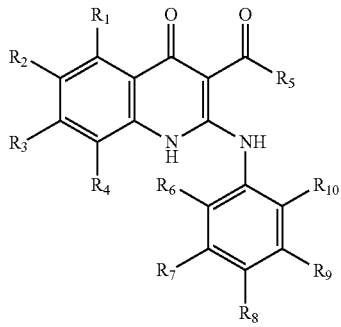

wherein, $R_1$ to $R_{10}$, each independently, are hydrogen, halogen, hydroxy, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl.

Preferably, $R_1$ to $R_{10}$ may, each independently, be hydrogen, halogen, nitro or $C_1$-$C_{12}$ alkyl.

More preferably, $R_1$ may be halogen or nitro, $R_2$ and $R_3$ may be hydrogen, $R_4$ may be halogen, $R_5$ may be $C_1$-$C_{12}$ alkyl, and $R_6$ to $R_{10}$ may be hydrogen, halogen or $C_1$-$C_{12}$ alkyl.

More preferably, the compound represented by the above Formula 1 may be selected from the following compounds 1 to 8:

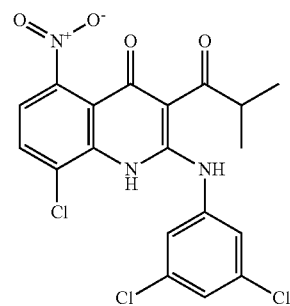

Compound 1

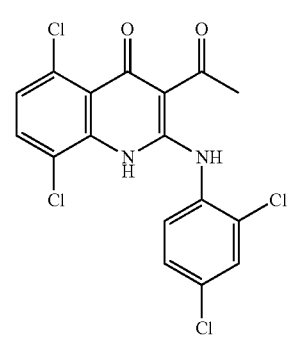

Compound 2

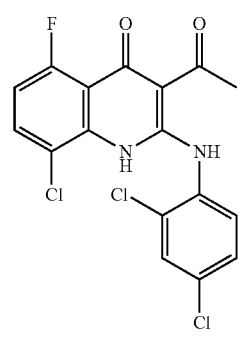

Compound 3

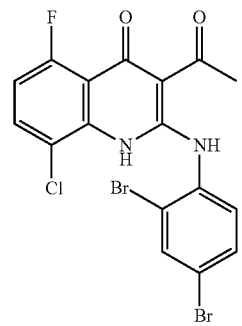

Compound 4

Compound 5

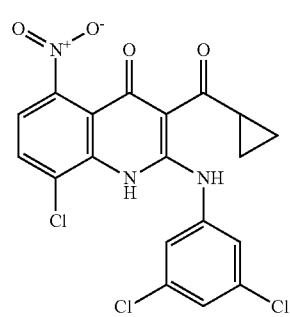

Compound 6

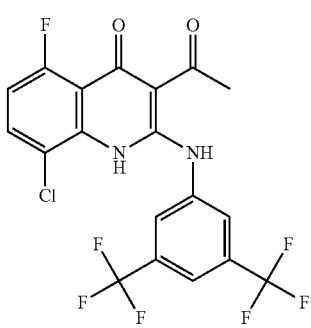

Compound 7

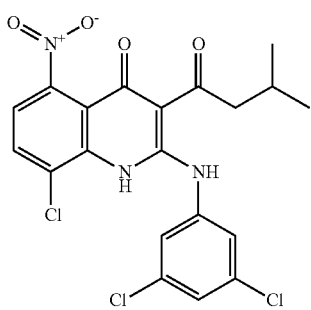

Compound 8

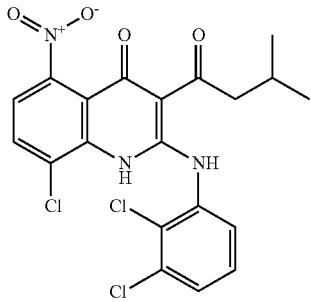

In the present invention, the DUSP1 inhibitor may be characterized by exhibiting an allosteric inhibitory effect.

Effects of the Invention

A pharmaceutical composition comprising a DUSP1 inhibitor according to the present invention can solve the problems of inhibitors that target an active site because it inhibits DUSP1 by an allosteric inhibitory mechanism, and are effective for preventing or treating diseases involving DUSP1 enzymes, for example, a cancer such as a liver cancer, a breast cancer and a pancreatic cancer, a hepatitis C, and a depression.

In particular, the DUSP1 inhibitor according to the present invention is very effective in treating a depression because it directly acts on neuronal growth.

BRIEF DESCRIPTION OF THE DRAWING(S)

FIG. 1 illustrates Lineweaver-Burke plot of Compound 2 according to an embodiment of the present invention.

FIG. 2 shows an image obtained by observing a neurite outgrowth effect of Compound 6 according to an embodiment of the present invention with a phase contrast microscope.

FIG. 3 shows results of the forced swimming behavior test according to an embodiment of the present invention.

FIG. 4 is a graph showing the change in tumor size using xenograft analysis method according to an embodiment of the present invention.

FORM FOR IMPLEMENTING THE INVENTION

Unless defined otherwise, all technical and scientific terms used herein have the same meaning as commonly understood by persons who has an ordinary skill in the art to which this invention belongs. In general, the nomenclature used herein is well known and commonly used in the art.

The present invention provides a DUSP1 inhibitor compound capable of inhibiting the activity of DUSP1 known to have an important effect on diseases such as a breast cancer, a pancreatic cancer, a hepatitis C, a depression and the like, and a pharmaceutical composition comprising this compound as an effective ingredient.

In the present invention, the DUSP1 inhibitor may include a compound represented by Formula 1:

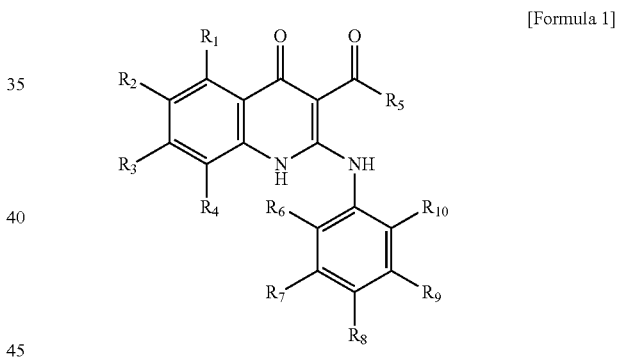

[Formula 1]

wherein, $R_1$ to $R_{10}$, each independently, are hydrogen, halogen, hydroxy, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl.

The compound represented by Formula 1 according to the present invention has inhibitory effect of an effective DUSP1 enzyme and promotion effect of a neuronal growth and does not exhibit the problem with the inhibitor targeting the enzyme active sites because the compound shows an allosteric inhibitory effect.

In the present invention, the term "allosteric inhibition" means that a specific substance binds to a site other than the active center (substrate binding site) of the enzyme protein, thereby causing a change in the three-dimensional structure of the enzyme and inhibiting the function of the enzyme.

In the present invention, the term "$C_1$-$C_{12}$ alkyl" means straight or branched saturated hydrocarbon group having 1 to 12 carbon atoms, preferably "straight or branched $C_1$-$C_4$ alkyl", which comprises lower alkyl such as methyl, ethyl, n-propyl, isopropyl, n-butyl, isobutyl and t-butyl. In a preferred embodiment of the present invention, the above alkyl may be alkyl in which at least one hydrogen is substituted by halogen, preferably chloro or fluoro, more preferably fluoro, e.g., $CF_3$.

In the present invention, the term "alkenyl" refers to straight or branched unsaturated hydrocarbon group having a specified carbon number, preferably straight or branched $C_2$-$C_6$ alkenyl, which is hydrocarbon group of 2 to 6 carbon atoms having at least one double bond, for example, ethenyl, propenyl, isopropenyl, butenyl, isobutenyl, t-butenyl, n-pentenyl and n-hexenyl.

In the present invention, the term "cycloalkyl" means cyclic hydrocarbon radical having a specified carbon number, preferably "$C_3$-$C_8$ cycloalkyl", which includes cyclopropyl, cyclobutyl and cyclopentyl.

In the present invention, the term "cycloalkenyl" means cyclic hydrocarbon group having a specified carbon number and containing at least one double bond, preferably "$C_5$-$C_7$ cycloalkenyl", and includes cyclopentene, cyclohexene and cyclohexadiene.

In the present invention, the term "alkyl amino" means alkyl having amino substituent.

In the present invention, the term "aryl" means substituted or unsubstituted monocyclic or polycyclic carbon ring which is totally or partially unsaturated, and is preferably monoaryl or biaryl. Preferably, the monoaryl has 5 to 6 carbon atoms, and the biaryl has 9 to 10 carbon atoms. Most preferably, the aryl is substituted or unsubstituted phenyl. When the monoaryl, for example phenyl, is substituted, the substitution may be made by various substituents at various positions, but may be preferably substituted with halogen, hydroxy, nitro, cyano, substituted or unsubstituted straight or branched $C_1$-$C_4$ alkyl, straight or branched $C_1$-$C_4$ alkoxy, alkyl-substituted sulfanyl, phenoxy, $C_3$-$C_6$ cycloheteroalkyl or a substituted or unsubstituted amino. When the aryl is biaryl, for example naphthyl, the substitution may be made by various substituents at various positions, and may be preferably substituted with halogen, hydroxy, nitro, cyano, substituted or unsubstituted straight or branched $C_1$-$C_4$ alkyl, straight or branched $C_1$-$C_4$ alkoxy, or substituted or unsubstituted amino, and more preferably substituted with alkyl-substituted amino.

In the present invention, the term "alkoxy" means a functional group in which an oxygen is bonded to an alkyl group.

In the present invention, the term "heteroaryl" is a heterocyclic aromatic group and comprises N, O or S as a heteroatom. Preferably, the heteroaryl is heterobiaryl containing N as a heteroatom.

In the present invention, the term "arylalkyl(aralkyl)" means an aryl group bonded to a chemical structure having one or more alkyl groups, preferably benzyl.

In the present invention, the term "alkylaryl" means an alkyl group bonded to a chemical structure consisting of one or more aryl groups.

In the present invention, the term "arylalkenyl" means an aryl group bonded to a chemical structure having one or more alkyl groups, preferably phenyl ethenyl.

According to a preferred embodiment of the present invention, $R_1$ to $R_{10}$ may, each independently, be hydrogen, halogen, nitro or $C_1$-$C_{12}$ alkyl.

According to a more preferred embodiment of the present invention, $R_1$ may be halogen or nitro, $R_2$ and $R_3$ may be hydrogen, and $R_4$ may be halogen, preferably Cl.

According to a more preferred embodiment of the present invention, $R_5$ may be $C_1$-$C_{12}$ alkyl.

According to a still more preferred embodiment of the present invention, $R_6$ to $R_{10}$ may be hydrogen, halogen or $C_1$-$C_{12}$ alkyl.

The most preferred compound that can be used as a DUSP1 inhibitor in the composition of the present invention is a compound having substituents as shown in following Table 1, among the compounds represented by Formula 1:

TABLE 1

| $R_1$ | $R_2$ | $R_3$ | $R_4$ | $R_5$ | $R_6$ | $R_7$ | R8 | $R_9$ | $R_{10}$ |
|---|---|---|---|---|---|---|---|---|---|
| $NO_2$ | H | H | Cl | isopropyl | H | Cl | H | Cl | H |
| Cl | H | H | Cl | $CH_3$ | H | H | Cl | H | Cl |
| F | H | H | Cl | $CH_3$ | Cl | H | Cl | H | H |
| F | H | H | Cl | $CH_3$ | Br | H | Br | H | H |
| $NO_2$ | H | H | Cl | cyclopropyl | H | Cl | H | Cl | H |
| F | H | H | Cl | $CH_3$ | H | $CF_3$ | H | $CF_3$ | H |
| $NO_2$ | H | H | Cl | isobutyl | H | Cl | H | Cl | H |
| $NO_2$ | H | H | Cl | isobutyl | Cl | Cl | H | H | H |

In the present invention, examples of the specific compounds that can be used as a DUSP1 inhibitor are as shown by following Compounds 1 to 8:

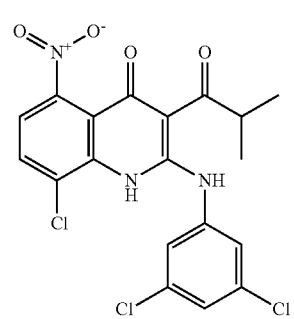

Compound 1

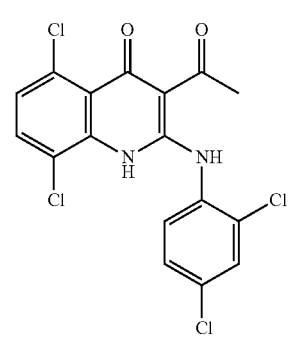

Compound 2

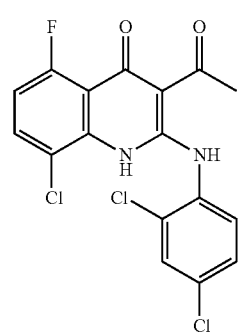

Compound 3

-continued

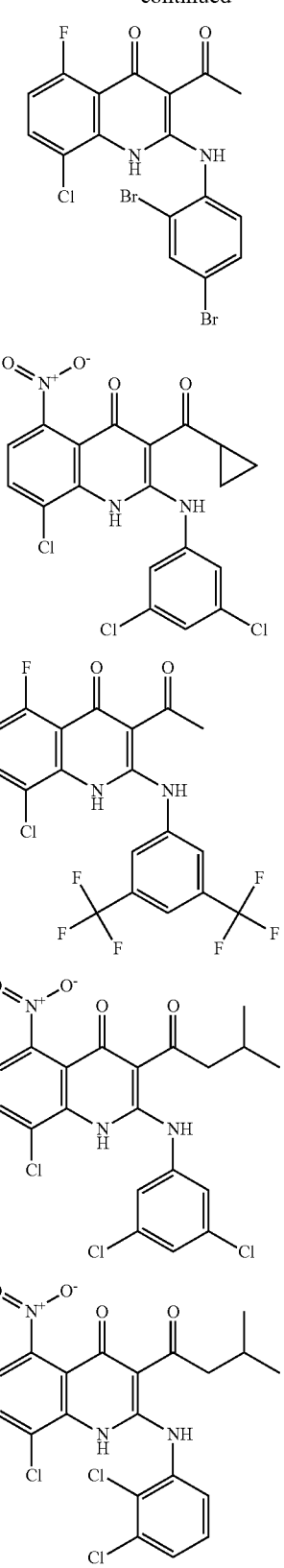

Compound 4

Compound 5

Compound 6

Compound 7

Compound 8

The compound represented by Formula 1 of the present invention can exhibit the effect of preventing or treating a depression, a hepatitis C, and a cancer such as a liver cancer, a breast cancer and a pancreatic cancer by inhibiting the activity of a DUSP1 enzyme with an allosteric activity inhibition mechanism.

Accordingly, the present invention provides a pharmaceutical composition for preventing or treating a depression, which comprises a DUSP1 inhibitor as an effective ingredient.

From an embodiment of the present invention, it has been confirmed that the DUSP1 inhibitor compound of the present invention can be effective in treating a depression by promoting neuronal growth, and also that it actually shows the mechanism of depression treatment through animal experiments.

The present invention also provides a pharmaceutical composition for preventing or treating a hepatitis C, which comprises a DUSP1 inhibitor as an effective ingredient.

The present invention also provides a pharmaceutical composition for preventing or treating a cancer, which comprises a DUSP1 inhibitor as an effective ingredient. The cancer may be a liver cancer, a breast cancer or a pancreatic cancer, but is not limited thereto, and includes all cancers that can be treated by inhibiting the DUSP1 activity. An embodiment of the present invention has confirmed that the use of the DUSP1 inhibitor of the present invention can effectively inhibit the liver cancer cells.

In the present invention, the DUSP1 inhibitor may include a compound represented by above Formula 1.

The pharmaceutical composition according to the present invention may comprise a pharmaceutically acceptable carrier thereof. The pharmaceutically acceptable carrier is one conventionally used in preparing the same, and includes a lactose, a dextrose, a sucrose, a sorbitol, a mannitol, a starch, an acacia rubber, a calcium phosphate, an alginate, a gelatin, a calcium silicate, a microcrystalline cellulose, polyvinylpyrrolidone, a cellulose, water, a syrup, methyl cellulose, methylhydroxybenzoate, propylhydroxybenzoate, a talc, magnesium stearate and a mineral oil, and the like, but is not limited thereto.

The pharmaceutical composition of the present invention may further comprise a lubricant, a wetting agent, a sweetener, a flavoring agent, an emulsifier, a suspension agent, a preservative, and the likes, in addition to the above components. The pharmaceutically acceptable carrier and formulation can be preferably prepared in accordance with each of the components using the method disclosed in *Remington's Pharmaceutical Sciences* (19th ed., 1995).

The pharmaceutical composition of the present invention can be administered orally or parenterally, and the parenteral administration includes intravenous injection, subcutaneous injection, intramuscular injection, intraperitoneal injection, transdermal administration, and the like.

The composition according to the present invention is administered in a pharmaceutically effective amount thereof. In the present invention, the term "pharmaceutically effective amount" means a sufficient amount to treat a disease at a reasonable benefit/risk ratio applicable to medical treatment, and an effective dosage level can be determined depending on a type of the patient's disease, a severity, an activity of the drug, a sensitivity for the drug, administration time, administration route, release rate, duration of treatment, factors involved in concurrently used drugs, and other factors well known in the medical arts. The composition according to the present invention may be administered as a separate therapeutic agent or in combination with other therapeutic agents, may be administered sequentially or simultaneously with conventional therapeutic agents, and be administered in a single dosage or multiple dosages. Taking all of the above factors into consideration, it is important to administer an amount that can obtain the maximum effect in a minimum amount without side effects, which can be easily determined by those skilled in the art.

Specifically, an effective dosage of the composition according to the present invention may vary depending on the age, sex and weight of the patient, and generally 0.001 to 150 mg per 1 kg of body weight, preferably 0.01 to 100 mg per 1 kg of body weight, can be administered daily or every other day, or divided into 1 to 3 times a day. However, the dosage may be increased or decreased depending on the administration route, sex, weight, age, etc., and thus the above dosage does not limit the scope of the present invention in any way.

The pharmaceutical composition of the present invention can be prepared in a unit dose form by formulating with a pharmaceutically acceptable carrier and/or an excipient or prepared by incorporating them into a multi-dose container, according to the methods which can be easily carried out by those skilled in the art. In this case, the formulation may be in the form of a solution, a suspension or an emulsion in an oil or an aqueous medium, or may be in the form of extracts, powders, granules, tablets or capsules, and the formulation may further include a dispersant or a stabilizer.

The compound of above Formula 1 itself as well as a pharmaceutically acceptable salt, a hydrate, a solvate or a prodrug thereof are used as an effective ingredient in the composition of the present invention.

In the present invention, the term "pharmaceutically acceptable salt" refers to salt of the compounds of above Formula 1 which have the desired pharmacological effect, i.e., the activity of inhibiting the proliferation of a vascular smooth muscle cell or the proliferation of a tumor cell. This salt can be formed using an inorganic acid such as hydrochloride, hydrobromide and hydroiodide, or an organic acid such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentanepropionate, digluconate, dodecyl sulfate, ethanesulfonate, fumarate, glucoheptanoate, glycerophosphate, hemisulfate, heptanoate, hexanoate, 2-hydroxyethanesulfate, lactate, maleate, methanesulfonate, 2-naphthalenesulfonate, nicotinate, oxalate, tosylate and undecanoate.

In the present invention, the term "pharmaceutically acceptable hydrate" refers to the hydrate of the compound of Formula 1 having the desired pharmacological effect.

In the present invention, the term "pharmaceutically acceptable solvate" refers to the solvate of the compound of Formula 1 having the desired pharmacological effect. The hydrate and solvate may also be prepared using the acids described above.

In the present invention, the term "pharmaceutically acceptable prodrug" refers to a derivative of the compound of Formula 1, which must be bioconverted before exerting the pharmacological effect of the compound of Formula 1. These prodrugs are generally prepared for chemical stability, patient compliance, bioavailability, organ selectivity, prescription convenience, sustained release and decrease of adverse effects. The prodrug of the present invention can be easily prepared using the compound of Formula 1 according to the method which is conventional in the art (e.g., Burger's Medical Chemistry and Drug Chemistry, 5th ed., 1: 172-178 and 949-982 (1995)).

EXAMPLES

Hereinafter, the present invention will be described in more detail with reference to the following examples. Since these examples are only intended to illustrate the invention, it will be apparent to those skilled in the art that the scope of the invention is not to be construed as limited by these examples.

Example 1: Screening of a Compound Inhibiting DUSP1 Activity

Enzyme potency assay method was used to discover a DUSP1 inhibitor. As a target compound for enzyme potency assay, about 6,000 kinds of compounds of the representative compound library provided by the compound bank of Korea Research Institute of Chemical Technology were used. A quinolinone compound was selected as the discovered mother nucleus, and about 250 kinds of compounds having the same backbones were divided again from the entire compound library to select compounds having excellent enzyme inhibitory function.

An allosteric inhibitor was searched by expressing and purifying the catalytic domain of DUSP1 protein. First, compounds that inhibit activity of a catalytic domain were selected, and then, among them, in order to find compounds having the allosteric inhibitory effect, the degree of competition between the active site inhibitor and the allosteric site inhibitor was measured by comparing change in the melting point of the proteins when bound to the compound and when not bound to the compound.

Eight (8) kinds of the allosteric inhibitor compounds compressed by the melting point analysis method are as follows:

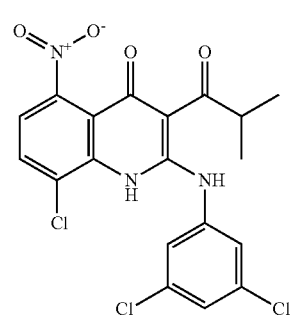

Compound 1

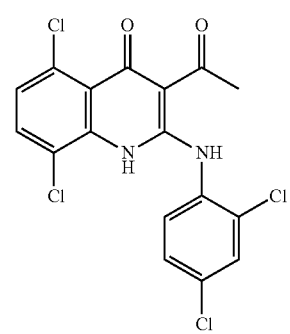

Compound 2

-continued

Compound 3

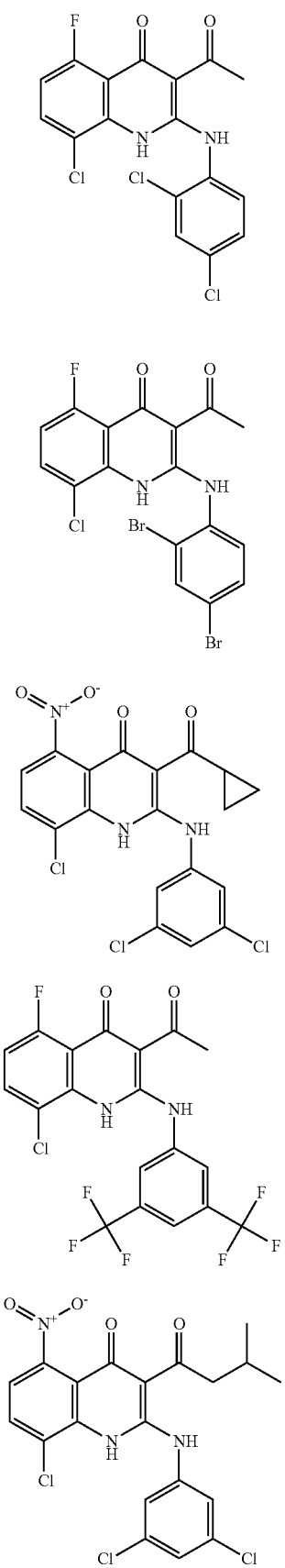

Compound 4

Compound 5

Compound 6

Compound 7

-continued

Compound 8

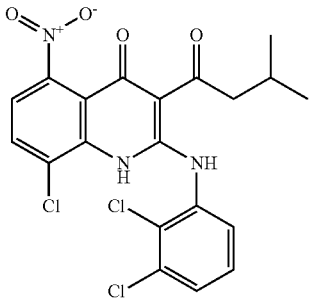

Example 2: Measurement of DUSP1 Activity Inhibitory Potency

The inhibitory potency of the DUSP1 activity on 8 kinds of the compounds screened in Example 1 was measured.

The fluorescence generated by the enzymatic reaction was measured by adding an assay buffer, a substrate and an enzyme protein to a 96-well microplate and then adding Compounds 1 to 8, respectively.

As the assay buffer, 20 mM Tris-HCl (pH 8.0), 0.01% Triton X-100 and 5 mM DTT were used, and a fluorescent substrate of 6,8-difluoro-4-methylumbelliferyl phosphate (DiFMUP) 10 μM was used as the substrate. The DUSP1 enzyme was expressed and purified from the activation domain (amino acid residues 166-316) and was used at 50 nM concentration in the enzyme reaction.

The expression and purification of the activation domain was carried out in the following manner. The DUSP1 activation domain (amino acid residues 166-316) was cloned into the pET28a (Novagen) vector and expressed in *E. coli* BL21 strain. The *E. coli* transformed with the expression vector of the DUSP1 activation domain was promoted with 0.1 mM of IPTG (isopropyl β-D-1-thiogalactopyranoside) at 37° C. The *E. coli* expressed with the DUSP1 activation domain was purified using a nickel affinity column after being crushed with a sonicator. The purified protein was quantified by the Bradford assay and used for the enzyme reaction.

Compounds 1 to 8 were dissolved in 100% DMSO (dimethyl sulfoxide) at a concentration of 5 mM to form a stock solution, and then added to the wells for the enzyme reaction such that it is adjusted to maintain a DMSO concentration of 5% in the enzyme reaction solution.

The fluorescence generated by the enzymatic action was measured using a Victor spectrofluorometer (PerkinElmer) with an excitation/emission wavelength of 355 nm/460 nm. From the obtained results, the intermediate suppression value ($IC_{50}$) was determined according to a 4-parameter logistic method of the Sigmaplot program package (Systat software Inc.), and the measurement results of the DUSP1 enzyme activity inhibitory potency were shown in Table 2 below.

TABLE 2

| | Compound | | | | | | | |
|---|---|---|---|---|---|---|---|---|
| | 1 | 2 | 3 | 4 | 5 | 6 | 7 | 8 |
| $IC_{50}$(μM) | 5.1 | 6.1 | 7.5 | 6.1 | 4.1 | 4.2 | 3.5 | 4.8 |

As can be seen from Table 2, the $IC_{50}$ values of Compounds 1 to 8 belong to the numerical ranges from 3.5 to 7.5 µM, which are lower than 10 µM, the $IC_{50}$ value of Sanguinarin known as the selective inhibitor of a conventional DUSP1, whereby it can be seen that the activity inhibitory potencies on the DUSP1 of Compounds 1 to 8 are very excellent.

In particular, the $IC_{50}$ values for Compounds 5 to 8 all are 5.0 µM or less, which indicates a very excellent DUSP1 inhibitory potency.

Example 3: Confirmation of Allosteric Inhibitory Mechanism

The Lineweaver-Burke plot was used to confirm that the above compounds have an allosteric inhibitory mechanism.

After Compound 2 was incubated in a 25 nM DUSP1 solution with final concentrations of 5, 7 and 10 µM for 5 min at a room temperature, DIFMUP was added to final concentrations of 50, 25, 12.5, 6.3, 3.1 and 1.6 µM to initiate the reaction and measure the fluorescence. The fluorescence was measured with an excitation/emission wavelength of 358 nm/460 nm using a Victor spectrofluorometer (PerkinElmer). The obtained values are shown in FIG. 1 using the following equation.

$$\frac{1}{V} = \frac{K_m + [S]}{V_{max}[S]} = \frac{K_m}{V_{max}} \frac{1}{[S]} + \frac{1}{V_{max}}$$

From FIG. 1, it was confirmed that the straight lines obtained when reacting with the concentration of the substrates different from each other intersect on the X-axis. It can be seen from the above that Compound 2 has the allosteric inhibitory mechanism and expected that Compounds 1 and 3 to 8, which have a chemical structure similar to Compound 2, also have the allosteric inhibitory mechanism.

Example 4: Measurement of Neuronal Differentiation

A neurite outgrowth assay was performed to confirm whether the DUSP1 inhibitor of the present invention is effective in treating a depression by promoting neuronal differentiation.

The Neurite outgrowth assay was carried out with PC12 neuron by appropriately modifying the protocol described in Ishima et al., (2015) Potentiation of neurite outgrowth by brexpiprazole, a novel serotonin-dopamine activity modulator: A role for serotonin 5-HT1A and 5-HT2A receptors. *Eur. Neuropsychopharm.* 25, 505-511.

The PC12 neurite cells were distributed by the Korea Cell Line Bank (Seoul National University in Korea) and prepared in a 96-well plate at a density of 7,000 cells/well. The cell culture was performed in Dulbeco's Modified Eagle's Media (DMEM), 10% FBS and 1% Anti-anti (Gibco). After culturing the prepared cells at 37° C. for 15 hours, Compounds 1 to 7 were added at a final DMSO concentration of 0.5% and a nerve growth factor (NGF) was added at a final concentration of 2.5 ng/ml when the medium was exchanged.

After 72 hours, the number and length of the neurite outgrowths were observed with a phase contrast microscope, and the results are shown in FIG. 2 (Compound 6) and Table 3 below. The Table 3 shows the concentrations at which stretching of the neurites begin to be clearly distinguished compared to the control groups and the results of evaluating the number and length of the neurites in high, middle and low through observation of a microscope, when the compounds were treated in the neurons.

TABLE 3

| Compound | Concentration of neurite outgrowth (µM) | Number and length of neurites |
| --- | --- | --- |
| 1 | 3.5 | middle |
| 2 | 2.5 | middle & high |
| 3 | 3.5 | middle |
| 4 | 3.5 | middle |
| 5 | 3.5 | middle |
| 6 | 0.6 | high |
| 7 | 0.6 | high |

As shown in FIG. 2, in the case of the control groups, the cell shape is mostly spherical, indicating that there is no significant change. However, in the case of the medium to which Compound 6 is added, the shape of neurites stretching from the cell can be confirmed. That is, it can be seen that the DUSP1 inhibitor of the present invention can act in the prevention and treatment of a depression by promoting differentiation of the neurons.

In addition, as can be seen from Table 3, Compounds 1 to 7 all induced neurite outgrowth, and Compounds 6 and 7 were evaluated as "high" in the length and number of the neurites even at very low concentrations (0.6 µM), which shows that it most effectively induces the neurite outgrowth.

In particular, Compound 7 showed the lowest $IC_{50}$ in the enzymatic reaction, that is, significantly excellent DUSP1 inhibitory potency compared to the other compounds (see Table 2). This means that the enzyme inhibitory activity and the neuronal differentiation potency were related with each other, and thus it can be seen that the DUSP1 inhibitor compound of the present invention is targeting the DUSP1 enzyme in cells.

Example 5: Animal Behavior Test for Depression Treatment

In order to evaluating anti-depressant potency through an animal behavior test, 5 male mice (5 weeks old) per cage, weighing 25 to 30 g, were stored at a control temperature of 23±1° C., and subjected to light/dark cycle for 12 hour. The tested mice were acclimated for 1 week.

In order to measure immobility time and swimming time according to the forced swimming behavior test, the tested mice were divided into two groups, with one group being examined by intraperitoneally administering Compound 2 at a concentration of 3.32 µg/g once a day for 9 days 30 minutes before the forced swimming behavior test.

The forced swim test (FST) is the most commonly used behavior test for forced swimming of an animal model with a depression by filling water of 10 cm into a transparent acrylic cylinder. In this case, the immobility posture of the mouse appears when giving up swimming in an environment that cannot escape from the water. As the immobility posture time increases, the state of the mouse shows a physiological change very similar to that of the depression of the human. Various existing pharmacological anti-depressants suppress this immobility posture time.

In order to measure the forced swim test (FST), 20 cm of water adjusted to a temperature of 23 to 25° C. was filled in a transparent beaker of 30 cm or more, and the tested mice were entered into the beaker and forced to swim for 6 minutes each on the first day and the 9th day of the drug administration. During 6 minutes of the forced swimming, the behaviors of the tested mice were recorded by dividing them into the immobility time and the swimming time.

In the graph of FIG. 3, the tested mice of the control group indicated that the immobility time which remained without any movement on the water surface increased greatly from 150 seconds on the first day to 225 seconds after 9 days. On the other hand, the tested mice treated with Compound 2 showed only a difference in the immobility time of about 10 seconds between the first day and the 9th day, meaning that the DUSP1 inhibitor of the present invention exhibited anti-depressant potency.

Example 6: Analysis of Liver Cancer Cell Growth Inhibition

The MTT analysis was performed to confirm the potency of inhibiting the growth of liver cancer cells of the DUSP1 inhibitor compound of the present invention.

A human liver cancer cell line Hep3B was cultured in DMEM, 10% FBS, 1% Anti-anti (Gibco) and prepared in a 96-well plate at a density of 7,000 cells/well. A normal hepatocyte line BNL-CL2 cell was cultured in DMEM, 10% FBS, 1% Anti-anti (Gibco) and prepared in a 96-well plate at a density of 3,000 cells/well.

After incubating at 37° C. for 15 hours, Compounds 6 to 8 were treated at the time of medium exchange so that final concentrations of the compounds in the medium become 2.5 µM and 5.0 µM, respectively, and the treatment conditions were adjusted so that the final DMSO concentration in the medium after treatment of the compounds can be maintained to 0.5%.

After 96 hours, a cell growth rate was measured using the Roche Cell Outgrowth Assay I (MTT) Kit. 10 µL of the MTT solution was added to each of 100 µL wells to a final concentration of 0.5 mg/ml, and then incubated at 37° C. for 4 hours and 100 µL of the solubilization buffer provided in the Kit was added. After 15 hours have elapsed, the absorbance was measured at 570 nm and the measurement results were shown in Table 4 below.

TABLE 4

| Compound | HEP3B cell line | | BNL-CL2 cell line | |
|---|---|---|---|---|
| | Compound concentration (5.0 µM) | Compound concentration (2.5 µM) | Compound concentration (5.0 µM) | Compound concentration (2.5 µM) |
| 6 | 14 | 18 | 8 | 111 |
| 7 | 27 | 40 | 125 | 156 |
| 8 | 16 | 15 | 54 | 139 |
| control | 106 | 104 | 107 | 95 |

In the above Table 4, in case Compounds 6 to 8 were used, it can be confirmed that the growth of the liver cancer cells (HEP3B cell line) were significantly inhibited compared to the normal hepatocyte control group (BNL-CL2 cell line). From the above, it can be seen that the DUSP1 inhibitor of the present invention is effective for the prevention or treatment of the liver cancer.

In particular, when the concentration of Compound 7 is 5.0 µM, Compound 7 showed no effect of the growth inhibition on the normal hepatocyte line, whereas it indicated a significant effect of the growth inhibition on the liver cancer cells. Accordingly, it can be seen that Compound 7 has a high possibility of being developed as the selective therapeutic agent of the liver cancer.

Example 7: Animal Test for Tumor Suppression

Using a xenograft assay method, it was confirmed whether the DUSP1 inhibitor of the present invention has the potency of inhibiting the cell growth of a liver cancer.

A human liver cancer cell line Hep3B of $1 \times 10^7$ was injected into the subcutaneous layer of the back of a nude mouse in DMEM medium, and then when the cell line was 200 to 500 $mm^3$ in size, it was extracted and inserted into the subcutaneous layer of the back of a new nude mouse in the size of 5×5×5 mm.

Compounds 7 and 8 were administered in the first dose when the cancer tissue had a sufficient size (200-500 $mm^3$) after transplantation, and the second dose was administered after measuring the size reduction of the tumor 4 days later.

The primary and secondary compounds 7 were administered intratumorally at concentrations of 3 µg and 6 µg, respectively, and the primary and secondary compounds 8 were administered intratumorally at concentrations of 2 µg and 4 µg, respectively.

After 4 days of the second administration, the size reduction of the tumor was measured, and the results were shown in FIG. 4.

In FIG. 4, it could be confirmed that the tumor size can be reduced by administering Compounds 7 and 8 into the cancer tissue, whereby Compound 7 reduces the tumor size by about 70% and Compound 8 reduces the tumor size by about 85%.

Therefore, it can be confirmed through animal tests that the DUSP1 inhibitor of the present invention can be substantially used for the treatment of cancer tissue.

As explained above, since specific portions of the contents of the present invention have been described in detail, it will be apparent to those skilled in the art that such specific techniques are merely preferred embodiments, and thus the scope of the present invention is not limited thereto. Accordingly, the substantial scope of the present invention will be defined by the appended claims and their equivalents.

What is claimed is:
1. A method for treating a depression, which comprises administering a DUSP1 inhibitor comprising a compound of Formula 1 to a patient suffering from the depression:

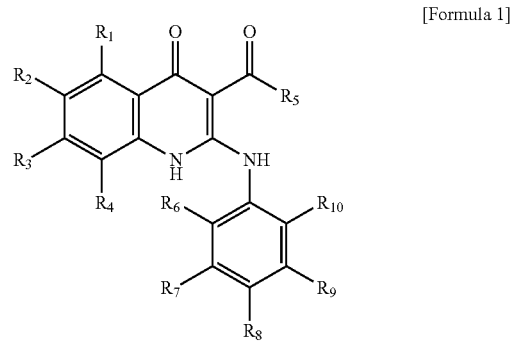

[Formula 1]

wherein, $R_1$ to $R_{10}$, each independently, are hydrogen, halogen, hydroxy, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl, or alkylaryl.

2. The method for or treating a depression according to claim 1, wherein $R_1$ to $R_4$, each independently, are hydrogen, halogen, cyano, nitro, $C_1$-$C_{12}$ straight alkyl, $C_3$-$C_{12}$ branched alkyl, $C_3$-$C_8$ cycloalkyl, $C_1$-$C_6$ trihaloalkyl, $C_1$-$C_6$ alkoxy, $C_1$-$C_6$ alkoxy substituted with halogen atom, aryl, heteroaryl, or arylalkyl, $R_5$ is $C_1$-$C_{12}$ straight alkyl, $C_3$-$C_{12}$ branched alkyl, or $C_3$-$C_8$ cycloalkyl, and $R_6$ to $R_{10}$, each independently, are hydrogen, halogen, cyano, nitro, $C_1$-$C_{12}$ straight alkyl, $C_3$-$C_{12}$ branched alkyl, $C_3$-$C_8$ cycloalkyl, $C_1$-$C_6$ trihaloalkyl, $C_1$-$C_6$ alkoxy, or $C_1$-$C_6$ alkoxy substituted with halogen atom.

3. The method for treating a depression according to claim 2, wherein $R_1$ to $R_4$, each independently, are hydrogen, halogen, cyano, nitro, $C_1$-$C_6$ straight alkyl, $C_3$-$C_6$ branched alkyl, $C_3$-$C_8$ cycloalkyl, $C_1$-$C_3$ trihaloalkyl, $C_1$-$C_3$ alkoxy, or $C_1$-$C_3$ alkoxy substituted with halogen atom, $R_5$ is $C_1$-$C_6$ straight alkyl, $C_3$-$C_6$ branched alkyl, or $C_3$-$C_8$ cycloalkyl, and $R_6$ to $R_{10}$, each independently, are hydrogen, halogen, cyano, nitro, $C_1$-$C_6$ straight alkyl, $C_3$-$C_6$ branched alkyl, $C_3$-$C_8$ cycloalkyl, $C_1$-$C_3$ trihaloalkyl, $C_1$-$C_3$ alkoxy, or $C_1$-$C_3$ alkoxy substituted with halogen atom.

4. The method for treating a depression according to claim 1, wherein the compound of Formula 1 is selected from the group consisting of Compounds 1 to 8:

Compound 1

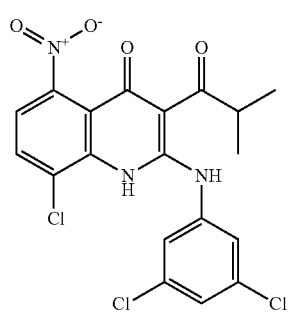

Compound 2

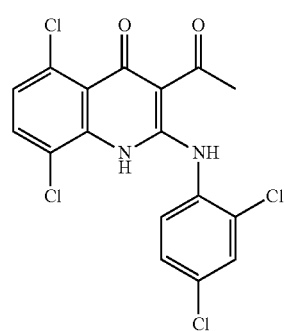

Compound 3

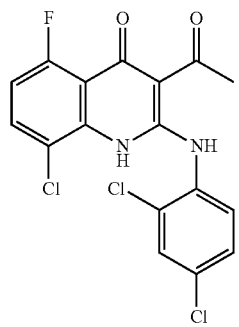

Compound 4

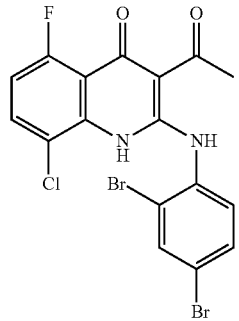

Compound 5

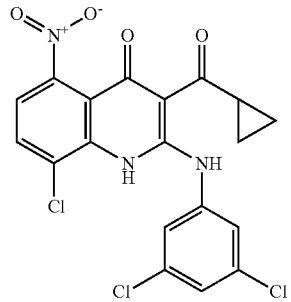

Compound 6

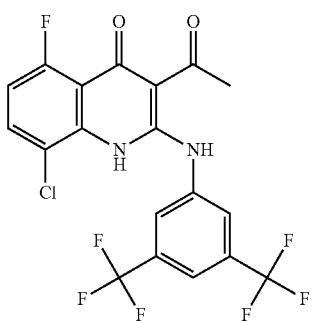

Compound 7

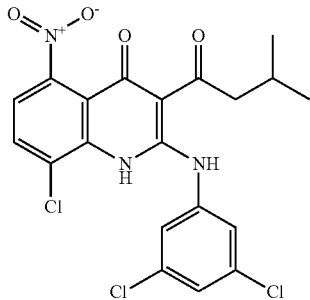

21
-continued

Compound 8

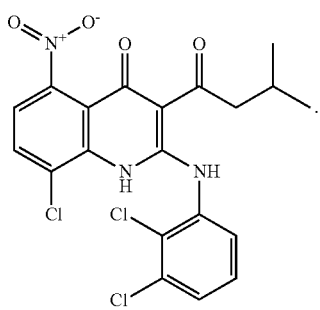

5. The method for treating a depression according to claim 1, wherein the DUSP1 inhibitor has an allosteric inhibitory potency.

6. A method for treating a hepatitis C in a subject in need thereof, which comprises administering a DUSP1 inhibitor comprising a compound selected from following Compounds 1 to 8 to the subject:

Compound 1

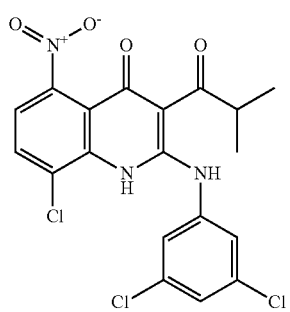

Compound 2

Compound 3

22
-continued

Compound 4

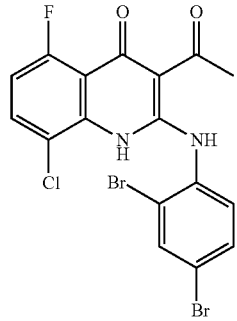

Compound 5

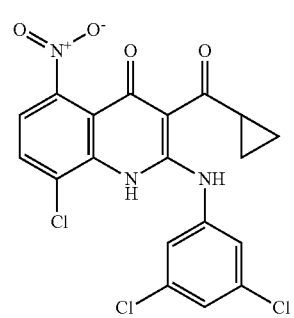

Compound 6

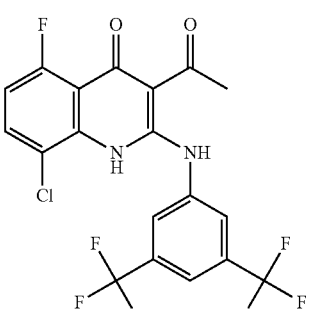

Compound 7

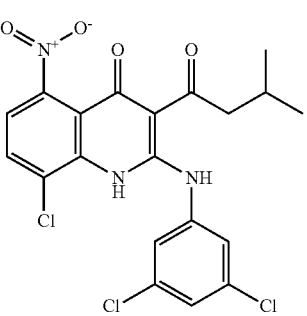

Compound 8

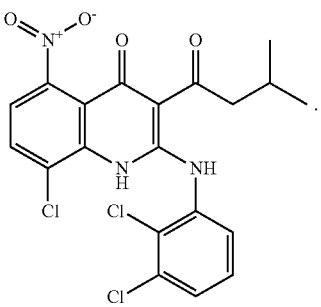

* * * * *